US012740536B2

(12) United States Patent
Wang et al.

(10) Patent No.: US 12,740,536 B2
(45) Date of Patent: Sep. 22, 2026

(54) LONG-STAPLE COTTON VARIETY ALLOWING SPINNING OF 150 N TO 340 N COMBED COTTON YARNS, AND BREEDING METHOD THEREOF

(71) Applicant: HENAN INSTITUTE OF SCIENCE AND TECHNOLOGY, Xinxiang (CN)

(72) Inventors: Qinglian Wang, Xinxiang (CN); Na Dong, Xinxiang (CN)

(73) Assignee: HENAN INSTITUTE OF SCIENCE AND TECHNOLOGY, Xinxiang (CN)

( * ) Notice: Subject to any disclaimer, the term of this patent is extended or adjusted under 35 U.S.C. 154(b) by 505 days.

(21) Appl. No.: 18/218,131

(22) Filed: Jul. 5, 2023

(65) Prior Publication Data

US 2024/0008437 A1 Jan. 11, 2024

(30) Foreign Application Priority Data

Jul. 6, 2022 (CN) ......................... 202210787608.8
May 29, 2023 (CN) ......................... 202310613485.0

(51) Int. Cl.
*A01H 6/60* (2018.01)
*A01H 1/02* (2006.01)

(52) U.S. Cl.
CPC ............... *A01H 6/604* (2018.05); *A01H 1/02* (2013.01)

(58) Field of Classification Search
CPC ................................. A01H 6/604; A01H 1/04
See application file for complete search history.

(56) References Cited

FOREIGN PATENT DOCUMENTS

AU 2020103667 A4 * 1/2021 ............... A01K 1/04

OTHER PUBLICATIONS

GB/T 20392-2006, Test method of properties of cotton fibers by high volume instruments, 2006, pp. 1-5.

* cited by examiner

*Primary Examiner* — David H Kruse
(74) *Attorney, Agent, or Firm* — Bayramoglu Law Offices LLC

(57) ABSTRACT

A long-staple cotton variety allowing spinning 150 N to 340 N combed cotton yarns, and a breeding method thereof are provided. In the present disclosure, through a "radiation mutagenesis of *Gossypium barbadense* (*G. barbadense*) L.+distant crossing of Chinese *G. barbadense* L. and Egyptian *G. barbadense* L. with upland cotton+backcrossing+*G. barbadense* L. and upland cotton introgression+stepped composite crossing" technology, four excellent parents are subjected to convergent crossing to obtain a long-staple cotton variety. During the selective breeding, through "radiation mutagenesis-screening-distant crossing-backcrossing-selfing-screening-crossing-screening" and "southern breeding+northern breeding", a large number of excellent genes are combined and aggregated; and through distant crossing of *G. barbadense* L. and upland cotton, backcrossing, and *G. barbadense* L. and upland cotton introgression, cell nuclei of *G. barbadense* L. effectively interact with cytoplasm of upland cotton.

7 Claims, 2 Drawing Sheets

LONG-STAPLE COTTON VARIETY ALLOWING SPINNING OF 150 N TO 340 N COMBED COTTON YARNS, AND BREEDING METHOD THEREOF

CROSS REFERENCE TO THE RELATED APPLICATIONS

This application is based upon and claims priority to Chinese Patent Applications No. 202210787608.8, filed on Jul. 6, 2022, and No. 202310613485.0, filed on May 29, 2023.

TECHNICAL FIELD

The present disclosure belongs to the technical field of selective breeding of cotton varieties, and in particular relates to a long-staple cotton variety allowing spinning 150 N to 340 N combed cotton yarns, and a breeding method thereof.

BACKGROUND

Long-staple cotton is a raw material for the spinning high-count yarns and special development industries. With the improvement of people's living standards and the rapid development of modern spinning technology, demands for long-staple cotton outside China continue to increase. Long-staple cotton is named for its long fibers and is also known as *Gossypium barbadense* (*G. barbadense*) L., and has a genome of AADD. Long-staple cotton originates from South America. Major international production areas of long-staple cotton mainly include Egypt, Sudan, Central Asia, the United States, Morocco, and the like.

Egypt, China, and the United States are major long-staple cotton producers worldwide. The long-staple cotton output for China is 28.1% of the total long-staple cotton output of the three countries. As special cotton for spinning high-grade yarns, high-quality long-staple cotton has a much higher price than ordinary upland cotton and ordinary long-staple cotton in China, and has always been in short supply on the international market. 80% or more of the superior long-staple cotton required by Chinese enterprises needs to be imported. In addition, most of the long-staple cotton varieties bred in China can only be used to spin 120 N or less yarns due to fiber quality deviations, and have a low acceptance level in textile enterprises, and for 120 N or more high-grade yarns, China mainly relies on imports. Production advantages of China's long-staple cotton have not been fully utilized, and thus China's long-staple cotton has weak market competitiveness and low added values, which seriously plagues the healthy and sustainable development of the cotton industry and the high-end cotton spinning and clothing industry in China. However, there are many problems in long-staple cotton varieties and selective breeding thereof: 1. The general long-staple cotton varieties have poor blight resistance. 2. There is a shortage of long-staple cotton varieties for spinning high-grade yarns. 3. The selective breeding of long-staple cotton varieties is limited by parent sources of a narrow genetic basis, single breeding methods, and insufficient innovation, consequently making it difficult to breed a superior long-staple cotton variety.

SUMMARY

An objective of the present disclosure is to provide a long-staple cotton variety allowing spinning 150 N to 340 N combed cotton yarns, and a breeding method thereof.

In order to achieve the above objective, the present disclosure adopts the following technical solutions:

A breeding method of a long-staple cotton variety allowing spinning 150 N to 340 N combed cotton yarns is provided, including the following steps:

(1) crossing high-quality and high-*Verticillium* wilt-resistance *G. barbadense* L. radiation-mutant BMC0318 as a female parent with an $F_1$ hybrid obtained by crossing between a high-yield and high-blight-resistance upland cotton Xinluzhong 14 mutant BMLK052 and Giza 45 as a male parent to obtain an $F_1$ hybrid; conducting modified backcrossing with the $F_1$ hybrid as a female parent and the radiation-mutant BMC0318 as a male parent for three generations; harvesting hybrid seeds of first-generation modified backcrossing together; harvesting hybrid seeds of second-generation modified backcrossing separately, and conducting fiber detection and screening; harvesting hybrid seeds of third-generation modified backcrossing, and conducting fiber detection and target trait screening to obtain an individual $BC_3F_1$; and selfing the individual $BC_3F_1$ for 5 generations to obtain BMC049; and (2) crossing *G. barbadense* L. Xinhai 40 as a female parent with the BMC049 as a male parent, harvesting hybrid seeds of the crossing separately, and conducting fiber detection and screening to obtained a first-generation hybrid; and subjecting the first-generation hybrid to sealing-flower selfing for 6 generations to obtain an $F_7$ population, isolating the $F_7$ population, and screening out the long-staple cotton variety BMC69 allowing spinning 150 N to 340 N cotton yarns from the isolated population.

Further, the upland cotton Xinluzhong 14 mutant BMLK052 is bred as follows: cultivating a stem apex of upland cotton Xinluzhong 14 on a *Fusarium oxysporum* (*F. oxysporum*)-containing modified MS medium in a greenhouse, and after seedling establishment, transplanting a seedling in a field; and a specific breeding process of the upland cotton Xinluzhong 14 mutant BMLK052 is as follows: cultivating the upland cotton Xinluzhong 14 in a greenhouse until a second true leaf grows, cutting a stem apex, and cultivating the stem apex on the *F. oxysporum*-containing modified MS medium in a greenhouse; after seedling establishment, transplanting a seedling in a blight and *Verticillium* wilt mixed disease nursery to obtain $R_1$; screening a blight and *Verticillium* wilt-resistant individual with a blight index of less than 2.5, a *Verticillium* wilt index of less than 17.0, and a strong growth potential out from $R_1$, subjecting the individual to sealing-flower selfing at a full-bloom stage, and after maturation, screening out a dominant individual; sowing $R_2$ seeds in Sanya of Hainan in rows, conducting sealing-flower selfing, eliminating an individual with an upper-half fiber length of less than or equal to 29.50 mm, a specific strength at break of less than or equal to 29.50 cN/tex, or a micronaire value of more than 4.90, and screening out a blight and *Verticillium* wilt-resistant individual with a blight index of less than 2.2 and a *Verticillium* wilt index of less than 15.0; sowing $R_3$ seeds in an artificial heavy and uniform blight and *Verticillium* wilt mixed disease nursery of Xinxiang in rows, conducting sealing-flower selfing, eliminating an individual with an upper-half fiber length of less than or equal to 29.70 mm, a specific strength at break of less than or equal to 29.70 cN/tex, or a micronaire value of more than 4.80, and screening out a blight and *Verticillium* wilt-resistant individual with a blight index of less than 1.9 and a *Verticillium* wilt index of less than 13.0; sowing $R_4$ seeds in Sanya of Hainan in rows, conducting sealing-flower selfing, eliminating an individual with an upper-half fiber length of less than or equal to 29.90 mm, a specific strength at break of less than or equal to 29.90 cN/tex, or a micronaire value of more than 4.70, and screening out a blight and *Verticillium* wilt-resistant individual with a blight index of less than 1.7 and a *Verticillium* wilt index of less than 12.0; sowing $R_5$ seeds in an artificial heavy and uniform blight and *Verticillium* wilt mixed disease nursery of Xinxiang in rows, conducting sealing-flower selfing, eliminating an individual with an upper-half fiber length of less than or equal to 30.50 mm, a specific strength at break of less than or equal to 30.50 cN/tex, or a micronaire value of more than 4.65, and screening out a blight and *Verticillium* wilt-resistant individual with a blight index of less than 1.6 and a *Verticillium* wilt index of less than 11.8; sowing $R_6$ seeds in Sanya of Hainan in rows, conducting sealing-flower selfing, eliminating an individual with an upper-half fiber length of less than or equal to 30.90 mm, a specific strength at break of less than or equal to 30.80 cN/tex, or a micronaire value of more than 4.63, and screening out a blight and *Verticillium* wilt-resistant individual with a blight index of less than 1.5 and a *Verticillium* wilt index of less than 11.7; and sowing $R_7$ seeds in an artificial heavy and uniform blight and *Verticillium* wilt mixed disease nursery of Xinxiang in rows, conducting sealing-flower selfing, eliminating an individual with an upper-half fiber length of less than or equal to 30.10 mm, a specific strength at break of less than or equal to 30.90 cN/tex, or a micronaire value of more than 4.62, and finally screening out a high-blight and *Verticillium* wilt-resistance Xinluzhong 14 mutant BMLK052 with a growth duration of 137 d, a single-boll weight of 6.03 g, a lint percentage of 40.5%, a plant height of 76 cm, a 2.5% span length of 31.05 mm, a specific strength of 30.96 cN·tex, and a micronaire value of 4.6.

Further, during the selective breeding, for cultivation in a field starting from the $R_2$ generation, 2 rows are planted in each zone in a single-row sowing manner with a row spacing of 75 cm, a plant spacing of 12 cm, and a zone spacing of 100 cm; the *F. oxysporum*-containing MS medium is prepared as follows: preparing an *F. oxysporum* bacterial solution with 4,000 and 6,000 *F. oxysporum* spores per mL, and applying 0.4 mL of the *F. oxysporum* bacterial solution by a glass rod evenly on an MS medium; and the blight resistance corresponds to a blight index of 1.48 and the *Verticillium* wilt resistance corresponds to a *Verticillium* wilt index of 11.6.

Further, a mutagenesis process for preparing the radiation-mutant BMC0318 is as follows: in October 2001, selecting seeds of *G. barbadense* L. Xinhai 21, and irradiating the seeds with $^{60}$Co-γ rays at different doses of 150 Gy, 200 Gy, and 250 Gy in the Institute of Isotope Research, Henan Academy of Sciences, where each sample to be irradiated is individually packaged, labeled with an irradiation dose, and then placed on a sample tray; an irradiation source is lowered, a dose field is calibrated, the sample tray is placed at a designated position, and an irradiation dosimeter is arranged; and the irradiation source is raised, and the sample is irradiated for 30 min; in October 2001, sowing mutagenic seeds in an experimental field in Sanya of Hainan, where 2 rows are planted in each zone in a single-row sowing manner with a row spacing of 75 cm, a plant spacing of 12 cm, and a zone spacing of 100 cm; screening a disease-resistant individual with a strong growth potential at a full-bloom stage out from an $M_1$ population of *G. barbadense* L. under different treatments, subjecting the disease-resistant individual to sealing-flower selfing, and investigating agronomic traits; after maturation, harvesting seeds separately, conducting seed selection, and determining a fiber quality; in April 2002, sowing $M_2$ seeds in Korla of Xinjiang, and further screening out a disease-resistant individual; subjecting the disease-resistant individual to sealing-flower selfing, and investigating agronomic traits; and after maturation, harvesting seeds separately, conducting seed selection, determining a fiber quality, and screening out a high-quality disease-resistant individual, which is named radiation-mutant BMC0318.

Further, during the 6 generations of selfing in step (2), generations $F_2$ and $F_4$ are subjected to multi-ecological selection of low-generation large populations; generations $F_2$, $F_4$, and $F_6$ are subjected to stepped mean-balanced selection of fiber quality, during which a fiber quality is gradually improved in a stepped manner; and generations $F_2$, $F_4$, and $F_6$ are subjected to mean-balanced selection of disease resistance.

Along-staple cotton variety BMC69 is provided, where a fiber of the long-staple cotton variety has an average upper-half length of 37.81 mm, a uniformity index of 89.60%, a specific strength at break of 55.97 cN/tex, a micronaire value of 3.20, and a diameter of 10.20 μm.

The present disclosure has the following advantages: In the present disclosure, through a "radiation mutagenesis of *G. barbadense* L.+distant crossing of *G. barbadense* L. and Egyptian *G. barbadense* L. with upland cotton+backcrossing+*G. barbadense* L. and upland cotton introgression+stepped composite crossing" technology, four excellent parents are subjected to convergent crossing to obtain a long-staple cotton variety. During the selective breeding, through "radiation mutagenesis-screening-distant crossing-back-crossing-selfing-screening-crossing-screening", a large number of excellent genes are combined and aggregated; and through identification and screening of multi-ecological disease resistance, mean-balanced selection of fiber quality and blight and *Verticillium* wilt resistance, many years of southern breeding+northern breeding, and introgression of blight and *Verticillium* wilt-resistance and high-fiber-quality genes of *G. barbadense* L. and upland cotton, cell nuclei of *G. barbadense* L. effectively interact with cytoplasm of upland cotton, such that high-yield and high-blight-resistance genes of a high-blight and *Verticillium* wilt-resistance mutant BMLK052 of upland cotton Xinluzhong 14 are successfully transferred into the high-quality and high-*Verticillium* wilt-resistance *G. barbadense* L. BMC0318 to obtain a *G. barbadense* L. variety BMC69 with high blight and *Verticillium* wilt resistance and long, fine, and strong fibers. According to test results of the Cotton Quality Supervision, Inspection, and Test Center of the Ministry of Agriculture of China according to the GB/T 20392-2006 "Test Method of Properties of Cotton Fibers by High Volume Instruments", a fiber of the *G. barbadense* L. variety BMC69 has an average upper-half length of 37.81 mm, a uniformity index of 89.60%, a specific strength at break of 55.97 cN/tex, a micronaire value of 3.20, and a diameter of 10.20 μm. A fiber of the cotton variety Giza 45 has a length of 34.60 mm, a uniformity index of 85.60%, a specific strength at break of 42.80 cN/tex, a micronaire value of 3.24, and a diameter of 10.20 μm. The major indexes such as fiber length, specific strength at break, uniformity, micronaire value, and fiber diameter of the BMC69 have fully reached or exceeded these indexes of the Egyptian Giza 45. According to trial spinning results, fibers of the BMC69 can be used to spin 150 N to 340 N yarns. The BMC69 can be demonstrated and cultivated in long-staple cotton areas to improve the market competitiveness of high-quality high-grade long-staple cotton and textile and clothing.

DETAILED DESCRIPTION OF THE EMBODIMENTS

Meanings of BMC in the name of the variety of the present disclosure are as follows: B represents Baiquan Agricultural College (a predecessor of the Henan institute of science and technology (HIST)), M represents cotton, and C represents long-staple cotton. The genetic resources of parents involved in the present disclosure all are from the National Cotton Germplasm Bank of the Institute of Cotton Research (ICR), Chinese Academy of Agricultural Sciences (CAAS), Anyang, Henan.

EXAMPLE

Figure 1:
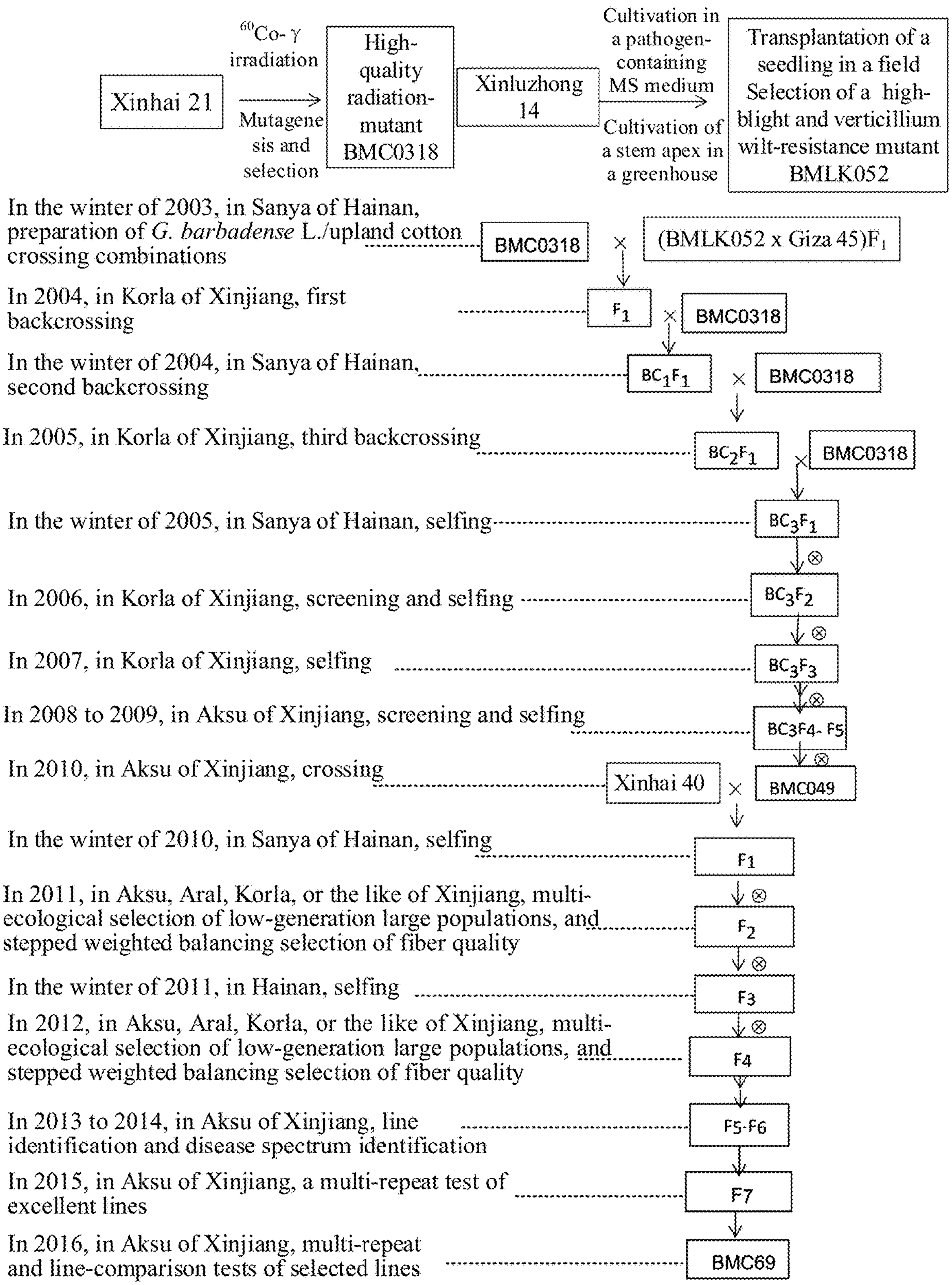
FIG. 1 is a flow chart of the breeding method of the present disclosure.
Figure 2:
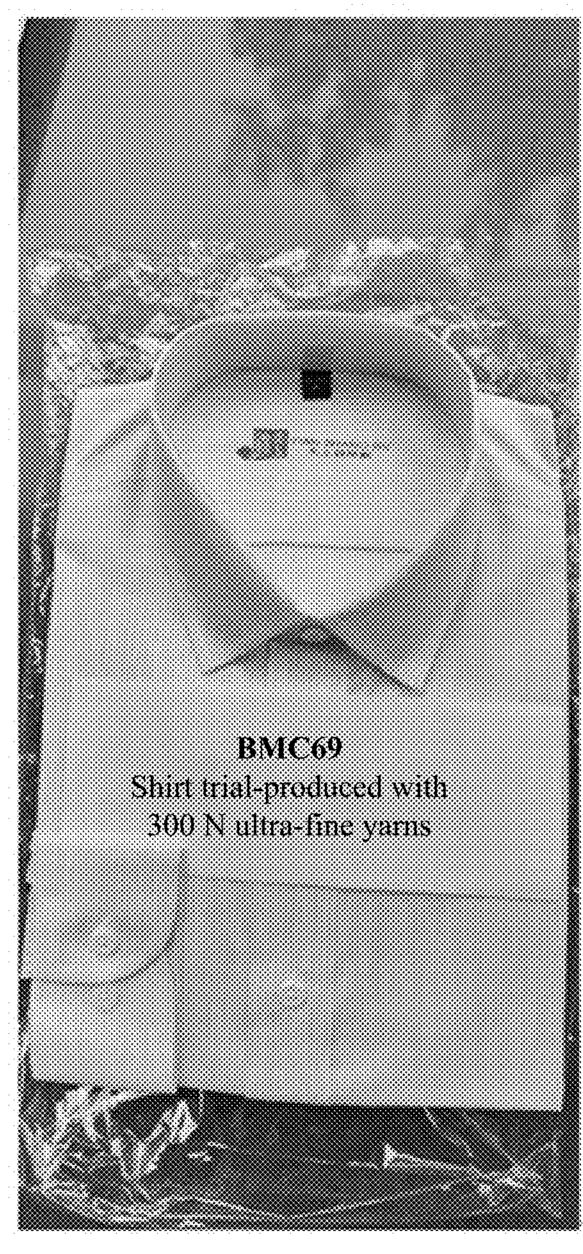
FIG. 2 shows a finished shirt made from the yarns of the present disclosure.

As shown in FIG. 1, a breeding method of a long-staple cotton variety allowing spinning 150 N to 340 N combed cotton yarns was provided, including the following steps: A stem apex of upland cotton Xinluzhong 14 was cultivated on an *F. oxysporum*-containing modified MS medium in a greenhouse, and after seedling establishment, a seedling was transplanted in a field, and specifically, a mutant was acquired by conducting seedling cultivation in a greenhouse, seedling establishment with a stem apex, screening in a blight and *Verticillium* wilt mixed disease nursery, and continuous stepped selection for upland cotton Xinluzhong 14. Specifically: Upland cotton Xinluzhong 14 seeds were first screened in a cultivation room with light and temperature controlled; in February 2000, full and consistent Xinluzhong 14 seeds were selected, soaked in water for 6 h, wrapped by a soaked 2-layer gauze, and subjected to accelerating germination in a 29° C. incubator for 35 h; after germination, seeds with consistent germination were selected, placed in pots each with a same mass of vermiculite, and further cultivated, where 2 cotton seedlings were cultivated in each pot at 26° C. to 28° C. during the day and 18° C. to 20° C. at night, with a light intensity of 2,500 lx and a daily light duration of 14 h; when a second true leaf of a cotton seedling grew, a stem apex was cut off by a sterile scalpel and cultivated on an *F. oxysporum*-containing MS medium (which was prepared as follows: an *F. oxysporum* bacterial solution with 4,000 to 6,000 *F. oxysporum* spores per mL was prepared, and 0.4 mL of the *F. oxysporum* bacterial solution was evenly applied by a glass rod on an MS medium) in a greenhouse; in April 2000, a seedling grown from the stem apex was transplanted in an artificial heavy and uniform blight and *Verticillium* wilt mixed disease nursery of Xinxiang; a blight and *Verticillium* wilt-resistant individual with a blight index of less than 2.5, a *Verticillium* wilt index of less than 17.0, and a strong growth potential was screened out from 287 $R_1$ individuals and subjected to sealing-flower selfing at a full-bloom stage, and agronomic traits were investigated; after maturation, seeds were harvested separately, seed selection was conducted, a fiber quality was determined, and 149 individuals were screened out; in October 2000, $R_2$ seeds were sown in Sanya of Hainan in rows, where 2 rows were planted in each zone in a single-row sowing manner with a row spacing of 75 cm, a plant spacing of 12 cm, and a zone spacing of 100 cm (same below); a disease-resistant individual was further screened out and subjected to sealing-flower selfing, and agronomic traits were investigated; after maturation, seeds were harvested separately, seed selection was conducted, and a fiber quality was determined; an individual with an upper-half fiber length of less than or equal to 29.50 mm, a specific strength at break of less than or equal to 29.50 cN/tex, or a micronaire value of more than 4.90 was eliminated, and 108 blight and *Verticillium* wilt-resistant individuals with a blight index of less than 2.2 and a *Verticillium* wilt index of less than 15.0 were screened out; in April 2001, $R_3$ seeds were sown in an artificial heavy and uniform blight and *Verticillium* wilt mixed disease nursery of Xinxiang in rows, a disease-resistant individual was further screened out and subjected to sealing-flower selfing, and agronomic traits were investigated; after maturation, seeds were harvested separately, seed selection was conducted, and a fiber quality was determined; an individual with an upper-half fiber length of less than or equal to 29.70 mm, a specific strength at break of less than or equal to 29.70 cN/tex, or a micronaire value of more than 4.80 was eliminated, and 53 blight and *Verticillium* wilt-resistant individuals with a blight index of less than 1.9 and a *Verticillium* wilt index of less than 13.0 were screened out; in October 2001, $R_4$ seeds were sown in Sanya of Hainan in rows, a disease-resistant individual was further screened out and subjected to sealing-flower selfing, and agronomic traits were investigated; after maturation, seeds were harvested separately, seed selection was conducted, and a fiber quality was determined; an individual with an upper-half fiber length of less than or equal to 29.90 mm, a specific strength at break of less than or equal to 29.90 cN/tex, or a micronaire value of more than 4.70 was eliminated, and 39 blight and *Verticillium* wilt-resistant individuals with a blight index of less than 1.7 and a *Verticillium* wilt index of less than 12.0 were screened out; in April 2002, $R_5$ seeds were sown in an artificial heavy and uniform blight and *Verticillium* wilt mixed disease nursery of Xinxiang in rows, a disease-resistant individual was further screened out and subjected to sealing-flower selfing, and agronomic traits were investigated; after maturation, seeds were harvested separately, seed selection was conducted, and a fiber quality was determined; an individual with an upper-half fiber length of less than or equal to 30.50 mm, a specific strength at break of less than or equal to 30.50 cN/tex, or a micronaire value of more than 4.65 was eliminated, and 21 blight and *Verticillium* wilt-resistant individuals with a blight index of less than 1.6 and a *Verticillium* wilt index of less than 11.8 were screened out; in October 2002, $R_6$ seeds were sown in Sanya of Hainan in rows, a disease-resistant individual was further screened out and subjected to sealing-flower selfing, and agronomic traits were investigated; after maturation, seeds were harvested separately, seed selection was conducted, and a fiber quality was determined; an individual with an upper-half fiber length of less than or equal to 30.90 mm, a specific strength at break of less than or equal to 30.80 cN/tex, or a micronaire value of more than 4.63 was eliminated, and 9 blight and *Verticillium* wilt-resistant individuals with a blight index of less than 1.5 and a *Verticillium* wilt index of less than 11.7 were screened out; in April 2003, $R_7$ seeds were sown in an artificial heavy and uniform blight and *Verticillium* wilt mixed disease nursery of Xinxiang in rows, a disease-resistant individual was further screened out and subjected to sealing-flower selfing, and agronomic traits were investigated; after maturation, seeds were harvested separately, seed selection was conducted, and a fiber quality was determined; an individual with an upper-half fiber length of less than or equal to 30.10 mm, a specific strength at break of less than or equal to 30.90 cN/tex, or a micronaire value of more than 4.62 was eliminated, and finally a high-blight (blight index: 1.48) and *Verticillium* wilt (*Verticillium* wilt index: 11.6)-resistance Xinluzhong 14 mutant BMLK052 with a growth duration of 137 d, a single-boll weight of 6.03 g, a lint percentage of 40.5%, a plant height of 76 cm, a 2.5% span length of 31.05 mm, a specific strength of 30.96 cN·tex, and a micronaire value of 4.6 was screened out. The excellent *G. barbadense* L. individual radiation-mutant BMC0318 as a female parent was crossed with $F_1$ of crossing between upland cotton and *G. barbadense* L. (BMLK052 X Giza 45) as a male parent to obtain an $F_1$ hybrid, and the $F_1$ hybrid as a female parent was backcrossed with the radiation-mutant BMC0318 as a male parent for three generations to obtain $BC_3F_1$; the $BC_3F_1$ was selfed for 5 generations to obtain BMC049; and Xinhai 40 as a female parent was crossed with the BMC049 as a male parent to obtain a first-generation hybrid, and the first-generation hybrid was subjected to sealing-flower selfing for 6 generations to finally obtain a long-staple cotton variety BMC69. During the selective breeding, generations $F_2$ and $F_4$ were subjected to multi-ecological selection of low-generation large populations, and generations $F_2$, $F_4$, and $F_6$ were subjected to stepped mean-balanced selection of fiber quality, that is, an individual or line with a fiber length and a fiber strength greater than an average fiber length and an average fiber strength of a population and with a fiber micronaire value and a fiber diameter smaller than an average fiber micronaire value and an average fiber diameter of the population was screened out, where a fiber quality was gradually improved in a stepped manner; and generations $F_2$, $F_4$, and $F_6$ were subjected to mean-balanced selection of disease resistance, that is, an individual or line with both a blight index and a *Verticillium* wilt index lower than an average blight index and an average *Verticillium* wilt index of a population was screened out. Mutagenesis of radiation-mutant BMC0318: in October 2001, seeds of *G. barbadense* L. Xinhai 21 were selected and irradiated with $^{60}$Co-γ rays at different doses of 150 Gy, 200 Gy, and 250 Gy in the Institute of Isotope Research, Henan Academy of Sciences, where each sample to be irradiated was individually packaged, labeled with an irradiation dose, and then placed on a sample tray; an irradiation source was lowered, a dose field was calibrated, the sample tray was placed at a designated position, and an irradiation dosimeter was arranged; and the irradiation source was raised, and the sample was irradiated for 30 min; in October 2001, mutagenic seeds were sown in an experimental field in Sanya of Hainan, where 2 rows were planted in each zone in a single-row sowing manner with a row spacing of 75 cm, a plant spacing of 12 cm, and a zone spacing of 100 cm; a disease-resistant individual with a strong growth potential at a full-bloom stage was screened out from an $M_1$ population of *G. barbadense* L. under different treatments, the disease-resistant individual was subjected to sealing-flower selfing, and agronomic traits were investigated; after maturation, seeds were harvested separately, seed selection was conducted, and a fiber quality was determined; in April 2002, $M_2$ seeds were sown in Korla of Xinjiang, and a disease-resistant individual was further screened out; the disease-resistant individual was subjected to sealing-flower selfing, and agronomic traits were investigated; and after maturation, seeds were harvested separately, seed selection was conducted, a fiber quality was determined, and a high-quality disease-resistant individual was screened out, which was named radiation-mutant BMC0318.

APPLICATION EXAMPLE

In the winter of 2003, in Sanya of Hainan, a high-quality and high-*Verticillium* wilt-resistance long-staple cotton radiation-mutant BMC0318 as a female parent was crossed with $F_1$ of crossing between high-yield and high-blight-resistance upland cotton and *G. barbadense* L. (BMLK052 X Giza 45) as a male parent.

In 2004, in Korla of Xinjiang, [BMC0318 X (BMLK052 X Giza 45) $F_1$] $F_1$ as a female parent was backcrossed with BMC0138 as a male parent to obtain BC1$F_1$, and seeds of the backcrossing were harvested together.

In the winter of 2004, in Sanya of Hainan, [BMC0318 X (BMLK052 X Giza 45) $F_1$] $BC_1F_1$ as a female parent was backcrossed with BMC0138 as a male parent to obtain $BC_2F_1$, seeds of the backcrossing were collected separately and subjected to fiber detection; and an individual with an upper-half fiber length of less than or equal to 35.00 mm, a specific strength at break of less than or equal to 47.00 cN/tex, a micronaire value of less than 3.03, or a micronaire value of more than 3.70 was eliminated.

In 2005, in Korla of Xinjiang, [BMC0318 X (BMLK052 X Giza 45) $F_1$] $BC_2F_1$ as a female parent was backcrossed with BMC0138 as a male parent, and seeds of the backcrossing were harvested separately and subjected to fiber detection; and individuals were compared in terms of traits such as plant type, fiber quality, single-plant boll formation, single-boll weight, lint percentage, and fruit-bearing shoot nodes to obtain a [BMC0138 X (BMLK052 X Giza 45) $F_1$] $BC_3F_1$ seed with excellent comprehensive traits.

In the winter of 2005, in Sanya of Hainan, the [BMC0318 X (BMLK052 X Giza 45) $F_1$] $BC_3F_1$ seed was sown and subjected to sealing-flower selfing; and seeds of the selfing were collected separately and subjected to fiber detection; and an individual with an upper-half fiber length of less than or equal to 36.00 mm, a specific strength at break of less than or equal to 48.00 cN/tex, a micronaire value of less than 3.30, or a micronaire value of more than 3.60 was eliminated.

In 2006, in Korla of Xinjiang, the [BMC0318 X (BMLK052 X Giza 45) $F_1$] $BC_3F_2$ seed was sown, non-disease-resistant individuals were eliminated, and disease-resistant individuals were subjected to sealing-flower selfing; seeds of the selfing were collected separately and subjected to fiber detection; and an individual with an upper-half fiber length of less than or equal to 36.00 mm, a specific strength at break of less than or equal to 48.00 cN/tex, a micronaire value of less than 3.30, or a micronaire value of more than 3.60 was eliminated.

In 2007, in Korla of Xinjiang, the [BMC0318 X (BMLK052 X Giza 45) $F_1$] $BC_3F_3$ seed was sown, non-disease-resistant individuals were eliminated, and disease-resistant individuals were subjected to sealing-flower selfing; seeds of the selfing were collected separately and subjected to fiber detection; and an individual with an upper-half fiber length of less than or equal to 36.00 mm, a specific strength at break of less than or equal to 49.00 cN/tex, a micronaire value of less than 3.30, or a micronaire value of more than 3.60 was eliminated.

In 2008, in Aksu of Xinjiang, the [BMC0318 X (BM1LK052 X Giza 45) $F_1$] $BC_3F_4$ seed was sown, non-disease-resistant individuals were eliminated, and disease-resistant individuals were subjected to sealing-flower selfing; seeds of the selfing were collected separately and subjected to fiber detection; and an individual with an upper-half fiber length of less than or equal to 36 mm, a specific strength at break of less than or equal to 49.00 cN/tex, a micronaire value of less than 3.30, or a micronaire value of more than 3.60 was eliminated.

In 2009, in Aksu of Xinjiang, the [BMC0318X (BM1LK052 X Giza 45) $F_1$] $BC_3F_5$ seed was sown, non-disease-resistant individuals were eliminated, and disease-resistant individuals were subjected to sealing-flower selfing; seeds of the selfing were collected separately and subjected to fiber detection; and an individual with an upper-half fiber length of less than or equal to 36.00 mm, a specific strength at break of less than or equal to 49.00 cN/tex, a micronaire value of less than 3.30, or a micronaire value of more than 3.50 was eliminated, and an individual with blight and *Verticillium* wilt resistance and high fiber quality was screened out and named BMC049.

In 2010, in Aksu of Xinjiang, a long-staple cotton variety Xinhai 40 with high quality and *Verticillium* wilt resistance as a female parent was crossed with the long-staple cotton variety BMC049 with blight and *Verticillium* wilt resistance and high fiber quality as a male parent.

In the winter of 2010, in Sanya of Hainan, $F_1$ (Xinhai 40 X BMC049) was sown and subjected to sealing-flower selfing; and seeds of the selfing were collected together.

In 2011, in Aksu, Aral, Korla, or the like of Xinjiang, $F_2$ (Xinhai 40 X BMC049) was sown and subjected to sealing-flower selfing, low-generation large populations were subjected to multi-ecological selection, and seeds were harvested separately and subjected to fiber detection and mean-balanced selection of fiber quality; and an individual with an upper-half fiber length of less than or equal to 37.00 mm, a specific strength at break of less than or equal to 51.00 cN/tex, a micronaire value of less than 3.20, or a micronaire value of more than 3.40 was eliminated.

In the winter of 2011, in Sanya of Hainan, $F_3$ (Xinhai 40 X BMC049) was sown and subjected to sealing-flower selfing; seeds of the selfing were collected separately and subjected to fiber detection; and an individual with an upper-half fiber length of less than or equal to 37.00 mm, a specific strength at break of less than or equal to 51.00 cN/tex, a micronaire value of less than 3.20, or a micronaire value of more than 3.40 was eliminated.

In 2012, in Aksu, Aral, Korla, or the like of Xinjiang, $F_4$ (Xinhai 40 X BMC049) was sown and subjected to sealing-flower selfing, low-generation large populations were subjected to multi-ecological selection and mean-balanced selection of fiber quality, and seeds were harvested separately and subjected to fiber detection; and an individual with an upper-half fiber length of less than or equal to 37.00 mm, a specific strength at break of less than or equal to 52.00 cN/tex, a micronaire value of less than 3.10, or a micronaire value of more than 3.30 was eliminated.

In 2013, in Aksu of Xinjiang, $F_5$ (Xinhai 40 X BMC049) was sown in a blight and *Verticillium* wilt mixed disease nursery; disease-resistant lines were screened out, and non-disease-resistant lines were eliminated; 20 individuals were randomly selected from each disease-resistant line and subjected to fiber detection; and lines with an upper-half fiber length of less than or equal to 37.00 mm, a specific strength at break of less than or equal to 54.00 cN/tex, a micronaire value of less than 3.10, or a micronaire value of more than 3.30 were eliminated.

In 2014, in Aksu of Xinjiang, $F_6$ (Xinhai 40 X BMC049) was sown in a blight and *Verticillium* wilt mixed disease nursery; disease-resistant lines were screened out, and non-disease-resistant lines were eliminated; 20 individuals were randomly selected from each disease-resistant line and subjected to fiber detection; and lines with an upper-half fiber length of less than or equal to 37.50 mm, a specific strength at break of less than or equal to 54.00 cN/tex, a micronaire value of less than 3.10, or a micronaire value of more than 3.30 were eliminated to obtain an excellent line.

In 2015, in Aksu of Xinjiang, $F_7$ (Xinhai 40 X BMC049) was sown, excellent lines were subjected to multi-repeat and line-comparison tests; non-disease-resistant lines were eliminated, and a disease-resistant line was subjected to sealing-flower selfing; and 20 individuals were randomly selected from each line and subjected to fiber detection.

In 2016, in Aksu of Xinjiang, selected lines were sown and subjected to multi-repeat and line-comparison tests. The lines were compared in terms of traits such as plant type, fiber quality, single-plant boll formation, lint percentage, single-boll weight, and disease resistance to obtain an excellent genetically-stable line 2 with prominent comprehensive traits of Xinhai 40 X {[high-quality and high-*Verticillium* wilt-resistance radiation-mutant BMC0318 X (high-blight and *Verticillium* wilt-resistance BMLK052 X Giza 45) $F_1$] $BC_3F_7$}, which was named BMC69. A fiber quality of the variety BMC69 was detected by the Cotton Quality Supervision, Inspection, and Test Center of the Ministry of Agriculture according to the GB/T 20392-2006 *"Test Method of Properties of Cotton Fibers by High Volume Instruments"*, and results were as follows (Table 1): the fiber had an average upper-half length of 37.81 mm, a uniformity index of 89.60%, a specific strength at break of 55.97 cN/tex, a micronaire value of 3.20, and a diameter of 10.20 μm. According to trial spinning results of China Resources Textile Co., Ltd., the fiber could be used to spin 150 N to 340 N extra-high-count yarns, and a strength of COMNE240 produced by the fiber was 21.0% higher than a strength of the Egyptian long-staple cotton Giza 87 (G87) and 13.0% higher than a strength of the American long-staple cotton PIMA.

TABLE 1

Test results of cotton fibers by the Cotton Quality Supervision, Inspection, and Test Center of the Ministry of Agriculture Test time: January 2018

| Variety name | Sampling site | Average upper-half length/mm | Uniformity index/% | Specific strength at break/ $cN \cdot tex^{-1}$ | Micronaire value | Diameter/ μm | Spinning uniformity index |
|---|---|---|---|---|---|---|---|
| BMC69 | Korla Aral | 37.81 | 89.60 | 55.97 | 3.20 | 10.20 | 250.00 |
| Giza 45 | Korla Aral | 34.60 | 85.60 | 42.80 | 3.24 | 10.20 | 184.00 |

Notes:

1. Testing basis: GB/T20392-2006 *"Test Method of Properties of Cotton Fibers by High Volume Instruments"*.

2. Main instrument: large-capacity fiber detector (ZXYQ 09-1).

TABLE 2

The genetic resource BMC69 has the following depository information at the China Center for Type Culture Collection (CCTCC) Depository.

| Genetic resource | Despot information |
| --- | --- |
| BMC69 | Deposit Accession Number: CCTCC NO: P202605<br>Date of deposit: March 30, 2026<br>Applicant (Depositor): HENAN INSTITUTE OF SCIENCE AND TECHNOLOGY<br>Name of Culture: Long-staple cotton seeds BMC69<br>Depository Institution: China Center for Type Culture Collection<br>Depository Institution Code: CCTCC<br>Address of Depository Institution: Wuhan University, No. 299 Bayi Road, Wuchang District, Wuhan City, Hubei Province, China |

The specific genetic resource BMC69 has been deposited under the Budapest Treaty and access to this deposit will be made available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer.

What is claimed is:

1. A seed of cotton variety *Gossypium barbadense* L. BMC69, wherein a representative seed of said variety was deposited under the China Center for Type Culture Collection (CCTCC), Wuhan University, Accession No. P202605.

2. A plant, or a regenerable part thereof, produced by growing the seed of claim 1.

3. A method of producing an F1 hybrid cotton seed, comprising the steps of crossing the plant of claim 2 with a different cotton plant and harvesting the resultant F1 hybrid cotton seed.

4. An F1 hybrid cotton seed produced by the method of claim 3.

5. An F1 hybrid cotton plant, or a regenerable part thereof, produced by growing the hybrid seed of claim 4.

6. A plant obtained by the vegetative reproduction of the cotton plant of claim 5.

7. A method of introducing a trait into cotton variety *Gossypium barbadense* L. BMC69 comprising:

(a) crossing a plant of variety BMC69 with a second plant comprising a desired trait to produce F1 progeny plants;

(b) selecting Fl progeny plants that have the trait to produce selected F1 progeny plants;

(c) crossing the selected progeny plants with at least a first plant of variety BMC69 to produce backcross progeny plants;

(d) selecting backcross progeny plants that have the trait and otherwise comprise all of the physiological and morphological characteristics of cotton variety BMC69 to produce selected backcross progeny plants; and (e) repeating steps (c) and (d) one or more times in succession to produce selected second or higher backcross progeny plants that comprise the trait and otherwise comprise all of the physiological and morphological characteristics of cotton variety BMC69 when grown in the same environmental conditions, wherein a sample of seed of cotton variety *Gossypium barbadense* L. BMC69 having been deposited under the China Center for Type Culture Collection (CCTCC), Wuhan University, Accession No. P202605.

* * * * *